United States Patent [19]

Hofer

[11] 4,443,616

[45] Apr. 17, 1984

[54] PRODUCTION OF 3-PYRROLIN-2-ONES

[75] Inventor: Peter Hofer, Liestal, Switzerland

[73] Assignee: The Purdue Frederick Company, Norwalk, Conn.

[21] Appl. No.: 256,169

[22] Filed: Apr. 21, 1981

Related U.S. Application Data

[63] Continuation of Ser. No. 12,496, Feb. 15, 1979, abandoned, and a continuation-in-part of Ser. No. 914,682, Jun. 12, 1978, abandoned.

[51] Int. Cl.$^3$ ............................................ C07D 207/38
[52] U.S. Cl. ..................................... 548/543; 548/551
[58] Field of Search .............. 260/326.5 FL; 548/543, 548/551

[56] References Cited

U.S. PATENT DOCUMENTS 3,272,842  9/1966  Easton et al. ...................... 548/543

OTHER PUBLICATIONS

Tyurenkov et al., Tr. Volgogr. Gos. Med. Inst., 31(3), pp. 35–39, (1979).

Primary Examiner—Paul M. Coughlan, Jr.
Assistant Examiner—David B. Springer
Attorney, Agent, or Firm—Steinberg & Raskin

[57] ABSTRACT

Pyrrolidin-2-ones are produced by hydrogenation of 3-pyrrolin-2-ones, which latter compounds could not prior to this invention be easily obtained. These 3-pyrrolin-2-ones with various substituents are produced by ring closure of N-aroylmethyl-acetamides. The ring closure is effected in basic media under nitrogen.

3 Claims, No Drawings

PRODUCTION OF 3-PYRROLIN-2-ONES

CROSS REFERENCE TO RELATED APPLICATION

This is a contination of application Ser. No. 12,496, filed Feb. 15, 1979, now abandoned and a continuation-in-part of my copending application Ser. No. 914,682, filed June 12, 1978, entitled "Production of Pyrrolidin-2-ones From 3-Pyrrolin-2-ones and the Production of 3-Pyrrolin-2-ones", now abandoned.

BACKGROUND OF THE INVENTION

Pyrrolidin-2-ones (I) of the formula:

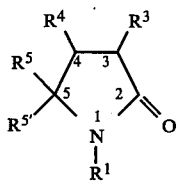
(I)

and their corresponding pyrrolidines (II) of the formula:

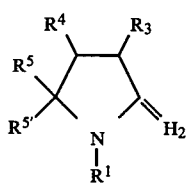
(II)

wherein $R^1$=hydrogen, alkyl, substituted alkyl, aryl, substituted aryl, acyl or aroyl; $R^3$=hydrogen, alkyl, substituted alkyl, aryl or substituted aryl; $R^4$=aryl, substituted aryl, alkyl or substituted alkyl; $R^5$=hydrogen, alkyl, substituted alkyl, aryl or substituted aryl; and $R^{5'}$=hydrogen, alkyl or substituted alkyl; include many known compounds exhibiting interesting CNS activity (Archivum Immunologiae et Therapiae Experimentalis 1975, 23, 733–751). Many of the compounds of Formula I above exhibit prostaglandin-like activity (Ger. Offen. No. 2,527,989).

The pyrrolidin-2-ones (I) have generally been prepared by ring closure of the corresponding 4-aminobutyric acid or ester (III) of the formula:

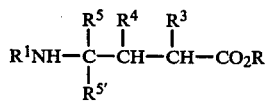
(III)

and 4-halogeno-butyramide, by reaction of lactones with amines, or hydrolysis of 2-imino-pyrrolidines (Brit. Pat. No. 1,350,582 and U.S. Pat. No. 4,012,495).

These methods of producing compounds of Formula I and II were limited as to efficiency, type of substituents in the various positions and difficulty of producing pure stereo- and optically active isomers.

SUMMARY OF THE INVENTION

Generally speaking, in accordance with this invention, 3-4-cis-substituted, optionally optically active, pyrrolidin-2-ones of Formula I, namely:

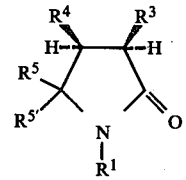
(I-cis)

or after isomerization

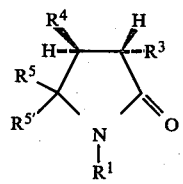
(I-trans)

are produced by hydrogenation of 3-pyrrolin-2-ones (V) of the formula:

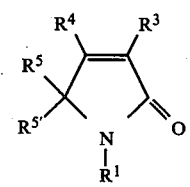
(V)

wherein $R^1$, $R^3$, $R^4$, $R^5$ and $R^{5'}$ have the same definitions as above, using the appropriate catalyst, optionally optically active (Angew. Chem. 83, 956 (1971)) or a built-in asymmetric center of C-5 of V, during hydrogenation.

One of the major difficulties in the production of the pyrrolidin-2-ones (I) by hydrogenation of the 3-pyrrolin-2-ones (V) is the difficulty of producing 3-pyrrolin-2-ones (V).

The present invention, therefore, further contemplates general methods of producing compounds of Formula V, and this is accomplished according to the invention by ring closure of N-aroylmethyl acetamides (IV) of the formula:

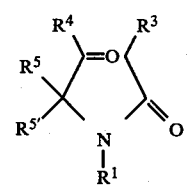
(IV)

to form the corresponding compound of Formula V. This ring closure is accomplished according to the invention under basic conditions, for example in t-butanol with potassium t-butoxide as base under nitrogen followed by acidification with a mineral acid such as HCl and dilution with water or by ring closure of the corresponding phosphonium bromide (XIII) of the formula:

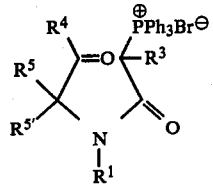

(XIII)

the ring closure being effected in basic medium to the corresponding compound of Formula V above.

The following definitions of terms are used herein:

Aroyl=Aryl—CO—

Acyl=Alkyl(minus 1 C)—CO—

Aryl=phenyl, pyridyl, furyl, thienyl, N-alkyl- or N-arylpyrrolyl, and the corresponding benzo derivatives, i.e. napthyl, quinolyl, etc.

Alkyl=$C_1$ to $C_{16}$ hydrocarbons

Substituents (up to 5 same or mixed)=alkyl, haloalkyl (e.g. $F_3C$), O-alkyl, N-dialkyl (same and different), S-alkyl, halogen, O-benzyl, N-dibenzyl, N-alkyl/benzyl, S-benzyl, O-aryl, S-aryl, N-diaryl, N-alkyl/benzyl/aryl, OH, $NH_2$, SH (the last three are protected during the basic ring closure)

Certain 3-pyrrolin-2-ones (V) are claimed in U.S. Pat. No. 3,272,842 prepared according to the following sequence:

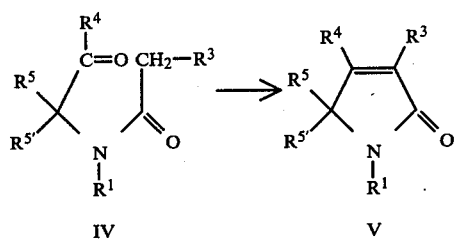

However $R^5$ and $R^{5'}$ exclude hydrogen and $R^4$ is always S—$CH_2$— (S=substituent). This ring closure of IV with $R^4$=aryl or substituted aryl and $R^5$ and/or $R^{5'}$=hydrogen according to the examples of U.S. Pat. No. 3,272,842 does either not proceed or yields yellow compounds (probably dimers), which is the result of the difference in substituents, i.e. the cited methods were not applicable to our compounds.

3-Pyrrolin-2-ones (V) have been produced (G. Stork and R. Matthews, Chemical Communications 1970, 445-6) in accordance with the following reaction sequence:

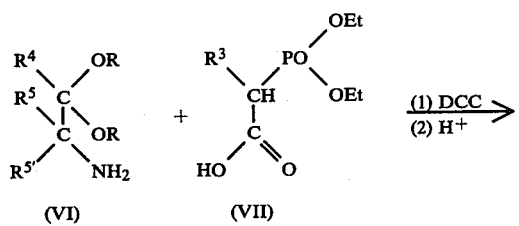

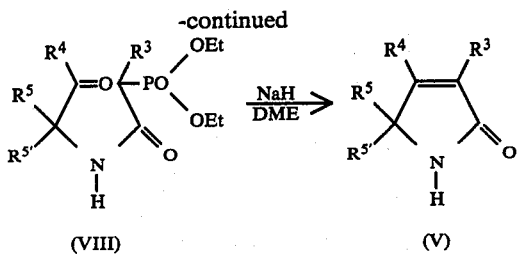

However, the use of dicyclohexylcarbodiimide (DCC) for the condensation of the aminoketone derivative (VI) with the unstable phosphonoacetic acid (VII) is unsuitable for large scale syntheses. In addition, the price of DCC is quite high, and the N,N'-dicyclohexylurea is a byproduct which is difficult to remove further makes the process uneconomical.

A similar ring closure reaction (T. W. Guntert et al. Helv. Chim. Acta 60, 334-9 (1977)) has been proposed as follows:

however, this process requires repeated chromatographic separation for the isolation of the 3-pyrrolin-2-one (V) with $R^4$=17β-steroidyl in 10% yield so that this process too is unsuitable for large scale synthesis, whereas they were unable to prepare the parent bromo compound of IX (corresponding to our XII).

In accordance with the present invention, direct ring closure of compounds of Formula IV can be effective, even for the synthesis of substituted 3-pyrrolin-2-ones (V) most conveniently where the substituents $R^1$ and $R^3$ of (IV) fulfill the following two criteria: (1) either $R^1 \neq H$, i.e. $R^1$=alkyl, substituted alkyl, aryl, substituted aryl, acyl or aroyl, or (2) if $R^1$=H, then $R^3$ is a group which stablizes anions at C-3 and is stable to bases, i.e. aryl, substituted aryl, carbonyl, etc., but not alkyl or hydrogen.

For the production of compounds of Formula V by ring closure in the case that $R^1$=hydrogen and $R^3$=hydrogen, alkyl, or substituted alkyl it has been found best to proceed in accordance with the following reaction sequence. Thus, where $R^4$=aryl, substituted aryl, $R^5$=hydrogen, alkyl or substituted alkyl and $R^{5'}$=hydrogen, alkyl or substituted alkyl it is possible to react to 2-amino-acetophenone (XI) of the formula:

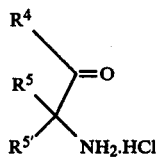

(XI)

with a 2-bromo-acyl chloride or bromide to form the corresponding bromo compound (XII) of the formula:

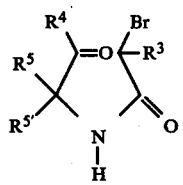

(XII)

in almost quantitative yield. The bromo compound XII contrary to the chloro compound IX reacts at room temperature with triphenylphosphine, e.g. in benzene solution, without decomposition to form the corresponding phosphonium bromide (XIII) of the formula:

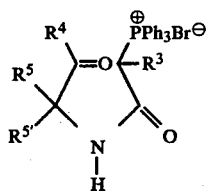

(XIII)

which is sufficiently soluble in alcohols and water for the ring closure reaction to the corresponding compound of Formula V above, e.g. with 2 N NaOH solution.

Thus, in accordance with this method, the starting aminoketones (XI) wherein $R^4$=aryl, substituted aryl, alkyl or substituted alkyl, $R^5$=hydrogen, alkyl or substituted alkyl, and $R^{5'}$=hydrogen or alkyl, are generally easily available compounds which can be acylated in practically quantitative yield in weakly basic media, e.g. sodium bicarbonate in an aqueous-ether mixture, with 2-bromoacyl chlorides or bromides to the corresponding N-(2-bromoacyl)-aminoketone (XII) wherein $R^3$=hydrogen, aryl, substituted aryl, alkyl or substituted alkyl.

The ketones of Formula XII as indicated above react at room temperature with triphenylphosphine, e.g. in benzene solution, to form the corresponding phosphonium bromide XIII which precipitates and can be collected by simple filtration. The solution of XIII in alcohol (preferably methanol) or water, and treatment with more than one equivalent of base (preferable 2 N NaOH solution) at room temperature quickly forms the desired 3-pyrrolin-2-one (V) and triphenylphosphinoxide in practically quantitative yield which precipitates from the solution. After dilution with water and evaporation of the alcohol, the mixture is collected and separated by extraction, e.g. with methylene chloride which removes the triphenylphosphine oxide.

The 3-pyrrolin-2-one (V) produced in any of the manners described above, can easily be hydrogenated with, e.g. Pd/C, Pt, or chiral rhodium complexes as catalyst in alcohol (preferably methanol) solution to the CNS active substituted pyrrolidine-2-ones (I-cis). This reaction sequence has the advantage that derivatives are obtained where in $R^3$ and $R^4$ are produced exclusively as cis substituents. The I-cis compounds may be converted to the corresponding I-trans compounds by base or acid treatment.

The pyrrolidine-2-ones (I) can be hydrolyzed by strong acid or base treatment to the corresponding 4-amino-butyric acid derivatives III accompanied by partial isomerization of the $R^3$ substituent resulting in a diastereoisomeric mixture which can be isolated as salts (e.g. HCl or sodium and magnesium etc.) or as free amino acids. The hydrolysis with $R^1$=alkyl is incomplete due to the formation of an equilibrium between I and III which can be separated by extraction.

An additional advantage of the present invention is that reduction of the new pyrrolidin-2-ones (I) e.g. with $B_2H_6$ or $LiAlH_4$ results in the formation of new pyrrolidines (II-cis ($R^3$ and $R^4$ cis) or II-trans ($R^3$ and $R^4$ trans)) depending upon the starting material.

The reduction of the C=C double bond in V is easily accomplished with hydrogen and about 5% to 15% of about 10% palladium on charcoal as catalyst. Asymmetric hydrogenation is obtained by chiral rhodium catalysts (e.g. J. Am. Chem. Soc. 1977, 99, 5946–52). Filtration and evaporation of the solvent, preferably methanol, directly yields the desired lactams I-cis in quantitative yield. In the case that $R^1$=benzyl in Formula V the I-cis with $R^1$=hydrogen can be obtained due to hydrogenolysis, i.e. the N-benzyl group has the function of a protecting group in the case that $R^3$=hydrogen, alkyl, or substituted alkyl.

Hydrolysis of I in refluxing concentrated (15–35%) mineral acids (e.g. HCl) followed by evaporation leads directly to the formation of the corresponding 4-aminobutyric acid hydrochlorides of Formula III in case of HCl. With sulfuric acid, the sulfates may be removed with barium hydroxide solution to obtain the free amino acids of Formula III which may be converted to a desired carbonic acid salt (e.g. magnesium) or to an ammonium salt with a therapeutically acceptable acid. On the other hand, hydrolysis with base leads to the corresponding carbonic acid salts (e.g. sodium, potassium).

Reduction of the carbonyl in lactams of Formula I with e.g. lithium aluminum hydride or boronhydride results in the formation of the corresponding pyrrolidines of Formula II which may be converted to an ammonium salt with a therapeutically acceptable acid.

DESCRIPTION OF PREFERRED EMBODIMENTS

The following examples are given to further illustrate the invention. The scope of the invention is not, however, meant to be limited to the specific details of the examples.

EXAMPLE 1

3,4-Diphenyl-3-pyrrolin-2-one (Va)

A solution of 12.6 g (50 mmoles) of 2-phenylacetamido-acetophenone in 200 ml of t-butanol is added to a refluxing solution of potassium t-butoxide prepared from 6.5 g of potassium (166 mmoles) and 200 ml of t-butanol under nitrogen. After 40 min of refluxing the solution is cooled to 40° C. and acidified with 2 N HCl (about 120 ml) to pH 6 to 5. The formed suspension is poured into 3 l of ice water. The precipitate is collected and washed with water. After drying 9.85 g (84.1%) of Va with mp 183°–90° C. are obtained. Extraction of the water with chloroform gave additional 1.3 g (11.1%) of Va. A recrystallized sample from benzene showed mp. 177°–9° C. The following compounds of structure V were prepared analogously:

3-Phenyl-4-(4′-chlorophenyl)-3-pyrrolin-2-one (Vb), mp 204°–10° C.
3-(2′-Carboxyphenyl)-4-phenyl-3-pyrrolin-2-one (Vc), mp 238°–41° C.
3-Phenyl-4-(4′-fluorophenyl)-3-pyrrolin-2-one (Vd), mp 200°–2° C.
3-(4′-Fluorophenyl)-4-phenyl-3-pyrrolin-2-one (Ve), mp 199°–209° C.
3-Phenyl-4-(4′-methylphenyl)-3-pyrrolin-2-one (Vf), mp 210°–20° C.
3-Phenyl-4-(4′-trifluoromethylphenyl)-3-pyrrolin-2-one (Vg), mp 195°–8° C.
3-(2′-Fluorophenyl)-4-(4′-trifluoromethylphenyl)-3-pyrrolin-2-one (Vh), mp 165°–6° C.
1,3,5-Trimethyl-4-phenyl-3-pyrrolin-2-one (Vi), mp 79°–81° C.
1-Benzyl-4-(4′-trifluoromethylphenyl)-3-pyrrolin-2-one (Vk), gum
1-Benzyl-3-methyl-4-(4′-trifluoromethylphenyl)-3-pyrrolin-2-one (Vl), gum
1,5-Dimethyl-3,4-diphenyl-3-pyrrolin-2-one (Vm), mp 95°–103° C.
1,5-Dimethyl-4-phenyl-3-pyrrolin-2-one (Vn), mp 130°–5° C.
1-Methyl-3-phenyl-4-(4′-methylphenyl)-3-pyrrolin-2-one (Vo), mp 123°–4° C.
3-Phenyl-4-(4′-methoxyphenyl)-3-pyrrolin-2-one (Vp), mp 179°–81° C.
3-Phenyl-4-(3′,4′-dimethoxyphenyl)-3-pyrrolin-2-one Vq), mp 202°–4° C.
3-(4′Fluorophenyl)-4-(4′-trifluoromethylphenyl)-3-pyrrolin-2-one (Vu), mp 212°–3° C.

EXAMPLE 2 cis-3,4-Diphenyl-pyrrolidin-2-one (cis-Ia)

A solution of 9.00 g of e,3,4-diphenyl-3-pyrrolin-2-one (Va) in 200 ml of methanol and 0.90 g of 10% palladium on charcoal are placed into a 500 ml hydrogenation flask and hydrogenated for 16 hr at room temperature. The catalyst is filtered off and the methanol evaporated in vacuo. Crystallization from benzene-petroliumether/1:1 gave crystals with mp 154°–5° C. The following compounds were prepared analogously:

3-Phenyl-4-(4′-fluorophenyl)-pyrrolidin-2-ones (cis-Id), mp 198°–200° C.
3-(4′-Fluorophenyl)-4-phenyl-pyrrolidin-2-one (cis-Ie), mp 167°–8° C.
3-Phenyl-4-(4′-methylphenyl)-pyrrolidin-2-one (cis-If), mp 190°–1° C.
3-Phenyl-4-(4′-trifluoromethylphenyl)-pyrrolidin-2-one (cis-Iq), mp 149°–51° C.
3-(2′-Fluorophenyl)-4-(4′-trifluoromethylphenyl)-pyrrolidin-2-one (cis-Ih), mp 154°–6° C.
1,3,5-Trimethyl-4-phenyl-pyrrolidin-2-one (cis Ii), gum
4-(4′-Trifluoromethylphenyl)-pyrrolidin-2-one (Ik), mp 121°–2° C.
3-Methyl-4-(4′-trifluoromethylphenyl)-pyrrolidin-2-one (cis-Il),
1,5 Dimethyl-4-phenyl-pyrrolidine-2-one (In), gum
1-Methyl-3-phenyl-4-(4′-methylphenyl)-pyrrolidin-2-one (cis-Io), mp 113°–4° C.
3-Phenyl-4-(4′-methoxyphenyl)-pyrrolidin-2-one (cis-Ip), mp 156°–9° C.
3-Phenyl-4-(3′,4′-dimethoxyphenyl)-pyrrolidine-2-one (cis-Iq), mp 144°–6° C.
3-(4′-Fluorophenyl)-4-(4′-trifluoromethylphenyl)-pyrrolidin-2-one (cis-Iu), mp 203°–4° C.

EXAMPLE 3

1,5-Dimethyl-4-(4′-nitrophenyl)-pyrrolidin-2-one (Ir)

4.32 g of In are gradually added to 30 ml of fuming nitric acid at −5° to 0° C. After 1 hr at −10° C. the solution was poured into 300 ml of water. Extraction with ethyl acetate and washing with bicarbonate solution and water gave after evaporation of the solvent 4.89 g (91.6%) of Ir. Crystallization from acetoneether/1:3 gave crystals with mp 94°–5° C.

EXAMPLE 4

1,5-Dimethyl-4-(4′-chlorophenyl)-pyrrolidin-2-one (It)

A solution of 4.89 g (20.9 mmoles) of Ir in 50 ml of methanol and 0.49 g of 10% palladium on charcoal are placed into a 250 ml hydrogenation flask and hydrogenated at room temperature for 30 hr. The catalyst is filtered off and the methanol evaporated in vacuo. The resulting 1,5-dimethyl-4-(4′-aminophenyl)-pyrrolidin-2-one (Is), isolated in 100% yield, is dissolved in 12 ml of 18% hydrochloric acid in a 250 ml beaker and dropwise treated with 5.23 ml of 4 N sodium nitrite solution at 0°–5° C. After 5 min at 0° C. the excess nitrite was destroyed with urea. After 10 min at 0°–5° C. the diazonium solution was added dropwise to a freshly prepared solution of CuCl (20.9 mmoles) in 8 ml of 37% hydrochloric acid at 0° C. A brown precipitate forms immediately which is warmed to 60° C. for 1 hr. Extraction with chloroform and washing with water gave 4.30 g of crude reaction product after evaporation. After filtration through 130 g of silicagel 3.80 g (81%) of It were recovered as a gum.

EXAMPLE 5

4-Amino-2-phenyl-3-(4′-trifluoromethylphenyl)-butyric acid hydrochloride (IIIg-HCl)

9.15 g of cis-Ig are suspended in 300 ml of 25% HCl solution in a 500 ml flask and refluxed for 13 hr. Dilution with 300 ml of water and evaporation in vacuo to dryness gave a crystalline white residue which was suspended in ether over night to remove any lactam. Filtration and washing with ether gave 9.65 g (89.4%) of IIIg-HCl with mp 182°–3° C.

Analysis calc. for $C_{17}H_{17}ClF_3NO_2 \cdot 0.5\ H_2O$ (368.8): found C,55.84%; H,4.96%; N, 3.79%; calc. C,55.37%;H,4.85%; N, 3.80%.

The following acid hydrochlorides were prepared analogously:

4-Amino-2,3-diphenyl-butyric acid-HCl (IIIa-HCl), mp 210°–22° C.
4-Amino-3-(4′-fluorophenyl)-2-phenyl-butyric acid-HCl (IIId-HCl), mp 190°–5° C.
4-Amino-2-(4′-fluorophenyl)-3-phenyl-butyric acid-HCl (IIIe-HCl), mp 170°–5° C.
4-Amino-3-(4′-methylphenyl)-2-phenyl-butyric acid-HCl (IIIf-HCl, mp 210°–6° C.
4-Amino-2-(2′-fluorophenyl)-3-(4′-trifluoromethylphenyl)-butyric acid-HCl (IIIh-HCl),mp 182°–5° C.
4-Amino-2-(4′-fluorophenyl)-3-(4trifluoromethylphenyl)-butyric acid-HCl (IIIu-HCl), mp 200°–3° C.
4-Amino-3-(4′-trifluoromethylphenyl)-butyric acid-HCl (IIIk-HCl), mp 175°–77° C.

4-Amino-2-methyl-3-(4'-trifluoromethylphenyl)-butyric acid-HCl (IIIl-HCl)
4-Methylamino-4-methyl-3-phenyl-butyric acid-HCl (IIIn-HCl), mp 165°–75° C.
4-Amino-3-(4'-methoxyphenyl-2-phenyl-butyric acid-HCl (IIIp-HCl), mp 190°–210° C.
4-Amino-3-(3',4'-dimethoxyphenyl)-2-phenyl-butyric acid-HCl (IIIg-HCl), mp. 230°–3° C.

EXAMPLE 6

3,4-Diphenyl-pyrrolidine (IIa)

A solution of 1.185 g of cis-3,4-diphenyl-pyrrolidin-2-one (Ia) in 30 ml of tetrahydrofuran (THF) is added slowly to a suspension of 0.950 g of lithium aluminum hydride (LAH) and refluxed for 7 hr. After cooling 5 ml of ethyl acetate are added to destroy the excess of LAH and 7 ml of water to form hydroxides. The suspension is filtered and washed with THF. The THF is removed in vacuo and the residue taken up into chloroform and extracted twice with 50 ml of 2 N sulfuric acid. The water phase is treated with 2 N NaOH solution until alkaline and extracted with chloroform. Crystallization of the residue from methylenechloride gave crystals with mp 169°–72° C. 0.05 ml of 37% HCl solution is added to a solution of 0.100 g of IIa dissolved in 3 ml of methanol. Evaporation and suspension in ether gave 0.111 g of IIa-HCl with mp 74°–84° C.

EXAMPLE 7

N-[(4'-Trifluoromethylbenzoyl)methyl]-2-bromoacetamide (XIIk)

A solution of 51.16 g (0.609 mole) of sodium bicarbonate in 550 ml of water is added under nitrogen at 0° to 10° C. to a two phase solution of 48.5 g (0.203 mole) of 2-amino-4'-trifluoromethylacetophenone hydrochloride (XIk) in 250 ml of water and 250 ml of ether. A second solution of 18.41 ml (0.223 mole) of bromoacetyl chloride in 200 ml of dry ether is added at 0° to 5° C. within 15 min to the above stirred suspension. The initially thick suspension becomes thinner. After 2 hr of stirring ethyl acetate is added until a clear two phase solution is obtained. The water is separated and the ethyl acetate-ether solution washed with water until neutral. Evaporation in vacuo gave 62.3 g (95%) of XIIk. A recrystallized sample had mp 201°–11° C.

EXAMPLE 8

N-[4'-Trifluoromethylbenzoyl)methyl]-2-(triphenyl-phosphonium bromide)-acetamide (XIIIk)

70.5 g (0.269 mole) of triphenylphosphin are added to a suspension of 62.36 g (0.192 mole) of XIIk in 600 ml of benzene. After 4 days of stirring at room temperature the solid is collected and suspended in 250 ml of acetone for 3 hr. Filtration gave 77.66 g (69% of XIIIk with mp 250°–1° C.

EXAMPLE 9

4-(4'-Trifluoromethylphenyl)-3-pyrrolin-2-one (Vk)

72.5 ml of 2 N NaOH solution are slowly added under nitrogen to a solution of 77.6 g (0.132 mole) of XIIIk in 780 ml of methanol to keep the temperature below 40° C. After 1 hr of stirring 15 ml of 2 N HCl solution are added to reach a pH of about 6.5. The methanol is partially evaporated in vacuo and after the addition of 200 ml of water removed completely. The precipitate is collected and washed with water. After drying the residue, weighing 67.25 g, is suspended in 200 ml of methylenechloride for 2 hr. Filtration gave 27.3 g (91%) of Vk with mp. 208°–20° C. (decomposition).

EXAMPLE 10

4-(4-Trifluoromethylphenyl)-pyrrolidin-2-one (Ik)

A solution of 27.2 g (0.12 mole) of Vk in 500 ml of methanol (partially suspended) is hydrogenated for 10 hr with 4.1 g of 10% Pd on charcoal as catalyst. Filtration and evaporation in vacuo gave 27.5 g (100% of Ik. A recrystallized (acetone-ether/1:2) sample has mp 121°–2° C.

Analysis ($C_{11}H_{10}F_3NO$): calc. C,57.64%; H,4.40%; N,6.11%; found C,57.65%; H,4.38%; N,6.35%.

EXAMPLE II

4-Amino-3-(4'-trifluoromethylphenyl)-butyric acid-HCl (IIIk-HCl)

11.45 g (50 mmoles) of Ik are refluxed for 15 hr in 100 ml of 25% HCl solution. After dilution with water and extraction with ether the water phase was evaporated in vacuo. The residue is suspended in little ether and collected: 13.45 g (95%) of IIIk-HCl with mp 175°–7° C.

Analysis ($C_{11}H_{13}ClF_3NO_2$): calc. C,46.57%; H,4.62%; N,4.94%; found C,46.44%; H,4.67%; N,5.06%.

While the invention has been illustrated with respect to the production of specific compounds by specific means, it is apparent that variations and modifications of the invention can be made.

What is claimed is:

1. Method of producing a 3-pyrrolin-2-one of the formula:

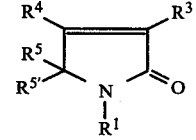

wherein $R^1$ is hydrogen, lower alkyl, phenyl or phenyl substituted by lower alkyl, $R^3$ is hydrogen, lower alkyl, phenyl, or phenyl substituted by halogen, carboxyl, lower alkyl, halo-lower-alkyl or lower alkoxy, with $R^3$ being other than hydrogen or alkyl when $R^1$ is hydrogen, $R^4$ is phenyl, or phenyl substituted by halogen, carboxyl, lower alkyl, halo-lower-alkyl or lower alkoxy, $R^5$ is hydrogen or lower alkyl, and $R^{5'}$ is hydrogen or lower alkyl, one of the substituents $R^5$ and $R^{5'}$ being hydrogen, which comprises the steps of refluxing under nitrogen, in the presence of equimolar amounts of KO C (CH3)3 in t-butanol a compound of the formula:

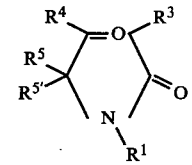

wherein $R^1$, $R^3$, $R^4$, $R^5$ and $R^{5'}$ have the same definitions as above, until the reaction is complete, acidifying the reaction mass, and separating the formed 3-pyrrolin-2-one therefrom.

2. Method according to claim 1 wherein the acidification is effected with HCl.

3. Method according to claim 2 wherein the acidified reaction medium is diluted with water.

* * * * *